(12) United States Patent
Vester et al.

(10) Patent No.: US 10,823,797 B2
(45) Date of Patent: Nov. 3, 2020

(54) APPARATUS AND METHOD FOR SPATIAL ENCODING USING A RADIO FREQUENCY SIGNAL IN MAGNETIC RESONANCE TOMOGRAPHY

(71) Applicant: Siemens Healthcare GmbH, Erlangen (DE)

(72) Inventors: Markus Vester, Nuremberg (DE); Ralf Kartäusch, Erlangen (DE); Matthias Gebhardt, Erlangen (DE); Peter Speier, Erlangen (DE)

(73) Assignee: Siemens Healthcare Gmbh, Erlangen (DE)

( * ) Notice: Subject to any disclaimer, the term of this patent is extended or adjusted under 35 U.S.C. 154(b) by 4 days.

(21) Appl. No.: 16/363,717

(22) Filed: Mar. 25, 2019

(65) Prior Publication Data

US 2019/0293739 A1 Sep. 26, 2019

(30) Foreign Application Priority Data

Mar. 26, 2018 (EP) ..................................... 18164022
May 9, 2018 (EP) ..................................... 18171548

(51) Int. Cl.
*G01R 33/46* (2006.01)
*G01R 33/48* (2006.01)
(Continued)

(52) U.S. Cl.
CPC .......... *G01R 33/4616* (2013.01); *A61B 5/055* (2013.01); *G01R 33/3875* (2013.01);
(Continued)

(58) Field of Classification Search
CPC ............ G01R 33/4616; G01R 33/3875; G01R 33/56563; G01R 33/4818; G01R 33/4836;
(Continued)

(56) References Cited

U.S. PATENT DOCUMENTS

| 4,777,441 A | 10/1988 | Foxall |
| 5,291,138 A | 3/1994 | Macovski |

(Continued)

FOREIGN PATENT DOCUMENTS

| DE | 19509020 A1 | 9/1996 |
| EP | 0284285 A2 | 9/1988 |
| WO | WO03016936 A1 | 2/2003 |

OTHER PUBLICATIONS

Duan, Qi, et al. "Improved Bloch-Siegert based B1 mapping by reducing off-resonance shift." NMR in Biomedicine 26.9 (2013): 1070-1078.

(Continued)

*Primary Examiner* — Susan S Lee
(74) *Attorney, Agent, or Firm* — Lempia Summerfield Katz LLC

(57) ABSTRACT

An apparatus and a method for spatial encoding in magnetic resonance tomography using a radio frequency signal are provided. A first set of parameters from a first frequency and from a first amplitude, and from a second frequency and a second amplitude is determined by the magnetic resonance tomograph, and corresponding signals are generated by a radio frequency device and transmitted by an antenna apparatus. A first gradient above the Larmor frequency of the nuclear spins is generated by the Bloch-Siegert effect. The same thing ensues with a second set of parameters that differs from the first set of parameters at least in one frequency or amplitude and therefore generates a second, different gradient.

18 Claims, 5 Drawing Sheets

20 = Control Unit
22 = Radio Frequency Unit
23 = Magnetic Resonance Tomograph Control
25 = Signal Bus
60 = Apparatus for Spatial Encoding

(51) Int. Cl.
*G01R 33/483* (2006.01)
*A61B 5/055* (2006.01)
*G01R 33/3875* (2006.01)
*G01R 33/565* (2006.01)
*G01R 33/34* (2006.01)
*G01N 24/08* (2006.01)

(52) U.S. Cl.
CPC ..... *G01R 33/4818* (2013.01); *G01R 33/4836* (2013.01); *G01R 33/56563* (2013.01); *G01N 24/08* (2013.01); *G01R 33/34* (2013.01); *G01R 33/4831* (2013.01); *G01R 33/5659* (2013.01); *G01R 33/56572* (2013.01)

(58) Field of Classification Search
CPC .......... G01R 33/56572; G01R 33/5659; G01R 33/34; G01R 33/4831; G01R 33/34046; G01R 33/341; G01R 33/385; A61B 5/055
See application file for complete search history.

(56) References Cited

U.S. PATENT DOCUMENTS

| | | | |
|---|---|---|---|
| 5,617,027 | A | 4/1997 | Decke |
| 6,037,775 | A * | 3/2000 | Shenoy ................ G01R 33/389 324/320 |
| 9,201,127 | B2 * | 12/2015 | Kumar ................ G01R 33/3628 |
| 9,952,296 | B2 * | 4/2018 | Krueger ................ G01R 33/285 |
| 2006/0232272 | A1 | 10/2006 | Hanley |
| 2009/0128155 | A1 | 5/2009 | Otake |
| 2012/0112748 | A1 | 5/2012 | Hetherington |
| 2015/0070014 | A1 * | 3/2015 | Biber ................ G01R 33/3415 324/309 |

OTHER PUBLICATIONS

European Search Report for European Patent Application No. 18171548.3-1022 dated Nov. 27, 2018.
Frimmer, Martin, and Lukas Novotny. "The classical Bloch equations." American Journal of Physics 82.10 (2014): 947-954.
Hasselwander et al.: "Bloch-Siegert Phase-Encoded MRI with a Single RF Coil and Frequency-Swept Pulses"; Proceedings of the International Society for Magnetic Resonance in Medicine, 25th Annual Meeting and Exhibition, Honolulu, HI, USA, Apr. 2017; vol. 5047.
Kartäusch, Ralf, et al. "Spatial phase encoding exploiting the Bloch-Siegert shift effect." Magnetic Resonance Materials in Physics, Biology and Medicine 27.5 (2014): 363-371.
Liimatainen, Timo, et al. "MRI contrast from relaxation along a fictitious field (RAFF)." Magnetic resonance in medicine 64.4 (2010): 983-994.
Liimatainen, Timo, et al. "MRI contrasts in high rank rotating frames." Magnetic resonance in medicine 73.1 (2015): 254-262.
Liimatainen, Timo, et al. "Relaxation dispersion in MRI induced by fictitious magnetic fields." Journal of Magnetic Resonance 209.2 (2011): 269-276.
Rabi, Isidor Isaac, et al. "Use of rotating coordinates in magnetic resonance problems." Reviews of Modern Physics 26.2 (1954): 167.
Sacolick, Laura I., et al. "B1 mapping by Bloch-Siegert shift." Magnetic resonance in medicine 63.5 (2010): 1315-1322.
Wan et al. "Phase Encoding with Bloch-Siegert effect using Parallel Transmit"; Proceedings of the International Society for Magnetic Resonance in Medicine, 25th Annual Meeting and Exhibition, Honolulu, HI, USA, Apr. 2017; vol. 1498.

* cited by examiner

20 = Control Unit
22 = Radio Frequency Unit
23 = Magnetic Resonance Tomograph Control
25 = Signal Bus
60 = Apparatus for Spatial Encoding

APPARATUS AND METHOD FOR SPATIAL ENCODING USING A RADIO FREQUENCY SIGNAL IN MAGNETIC RESONANCE TOMOGRAPHY

This application claims the benefit of EP 18164022.8, filed on Mar. 26, 2018, and EP 18171548.3, filed on May 9, 2018, which are hereby incorporated by reference in their entirety.

BACKGROUND

The present embodiments relate to an apparatus and a method for spatial encoding in a magnetic resonance tomograph.

Magnetic resonance tomographs are imaging apparatuses that, to represent an examination subject, align nuclear spins of an examination subject with a strong external magnetic field and excite an alternating magnetic field into precession around this alignment. The precession or return of the spins from this excited state into a state with lower energy in turn generates in response an alternating magnetic field (e.g., a magnetic resonance signal), which is received using antennas.

A spatial encoding may be imprinted on the signals with the aid of low frequency magnetic gradient fields, subsequently allowing the received signal to be assigned to a volume element. The received signal is then evaluated, and a three-dimensional imaging view of the examination subject is provided. The image generated indicates a spatial density distribution of the spins.

The gradient coils used are large, however, due to the fields required and the examination volume that is to be scanned. The gradient coils are configured to be electrically and mechanically robust because of the high currents and magnetic forces that occur. Due to the currents used, in the region of several hundred amperes, and the voltage of up to a kilovolt that is needed for this, applying the gradient is expensive and entails high energy costs. The waste heat is to be dissipated, and the magnetic fields with frequencies in the audible range cause unpleasant noises for the patient. These are particularly bothersome in examinations in the context of research, where the patient is not supposed to detect whether a magnetic resonance scan is currently in progress.

Due to the inductivity of the gradient coils, the maximum rate of increase in the current and hence the speed of the spatial encoding are likewise limited. This also applies to small local gradient coils, which may be arranged directly on the patient. These subject the patient to unpleasant vibrations.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an apparatus and a better method for spatial encoding, which is more agreeable for the patient and simpler in design, are provided.

The apparatus according to one or more of the present embodiments for spatial encoding in magnetic resonance tomography with a magnetic resonance tomograph includes a radio frequency unit configured to generate a first radio frequency signal with a first frequency and a second radio frequency signal with a second frequency of high output. A high output may be an output of more than 10 watts, 100 watts, or 1000 watts. Also regarded as being a high output is an output that is greater than 1%, 10%, 25%, 50%, or 100% of the output of an excitation pulse used to excite nuclear spins, with the first frequency and the second frequency being close to the Larmor frequency of the magnetic resonance tomograph. The term Larmor frequency defines the precession frequency of the nuclear spins to be acquired where there is a static magnetic field B0 of the field magnet in the examination region. 'Close to' is defined as a frequency spacing of less than 0.1%, 0.5%, 1%, or 5% of the Larmor frequency (e.g., a deviation of less than 1 kHz, 50 kHz, 100 kHz, 500 kHz, or 1 MHz), with the first frequency not being equal to the second frequency.

The apparatus further includes an antenna apparatus that is configured to emit the first radio frequency signal and the second radio frequency signal into an examination region of the magnetic resonance tomograph. The antenna apparatus may be arranged, for example, in or on the patient tunnel or may be arranged on the patient as a local coil.

The method according to one or more of the present embodiments is carried out on a magnetic resonance tomograph with an apparatus according to the present embodiments. The method determines in one act a first set of parameters consisting of a first frequency and a first amplitude, and a second frequency and a second amplitude using the magnetic resonance tomograph (e.g., by a control computer). The parameters are determined such that when transmitting signals according to the parameters over the antenna apparatus, a first gradient above the Larmor frequency of the nuclear spins is generated by the Bloch-Siegert effect. A gradient is defined as a first derivation of the Larmor frequency as a function of the location according to the location along a spatial direction.

The signals according to the first set of parameters are generated in a further act by a radio frequency unit and are radiated into the examination region using the antenna apparatus. In one embodiment, the radio frequency unit may be the same radio frequency unit with which the excitation pulses for the nuclear spins are also generated.

In a different act, a second set of parameters consisting of a third frequency and a third amplitude, and a fourth frequency and a fourth amplitude are determined by the magnetic resonance tomograph. The parameters in the second set of parameters are determined such that, when signals are transmitted according to the parameters over the antenna apparatus using the Bloch-Siegert effect, a second gradient is generated above the Larmor frequency of the nuclear spins. The first set of parameters and the second set of parameters differ in at least the first frequency and/or the first amplitude and/or second frequency and/or second amplitude of the first set from the third frequency and/or third amplitude and/or fourth frequency and/or fourth amplitude of the second set, respectively. The second gradient differs from the first gradient. The first gradient and the second gradient may have different directions (e.g., the vector of the first gradient and the vector of the second gradient enclose an angle that is not zero).

The signals according to the second set of parameters are generated by the radio frequency unit in a further act and radiated to the examination region by the antenna apparatus.

It is known from the Bloch-Siegert effect that a Larmor frequency, provided here by the static magnetic B0 field of a field magnet of the magnetic resonance tomograph at the location of the nuclear spins and the magnetic moment of the nuclear spins, may be shifted by an alternating magnetic field at this location by a frequency that is not equal to this local Larmor frequency in the frequency domain. The frequency shift is proportional to the square of the field strength of the alternating field and indirectly proportional to the difference in the frequencies of the correction signal and the local Larmor frequency. Therefore, from a target frequency shift in the Larmor frequency at a given location, a target field strength may be calculated as a function of the frequency of the correction signal, with which the Larmor frequency may be shifted at this location to the predetermined frequency. In this way, a target spatial field strength distribution may be determined or distribution over the examination area may be output, for example, to generate a linear frequency gradient of the Larmor frequency in one or a plurality of spatial directions.

In this way, the effect of the gradient coils in the spatial encoding using radio frequency signals may be emulated by a radio frequency apparatus. The effect is, for example, already present for excitation or may also be changed considerably faster than is the case with gradient coils that are limited by the maximum rate of increase.

In one embodiment, external influences that influence the local magnetic field have already been considered and compensated for. These may be, for example, leaps in the magnetic susceptibility that are caused by transitions between different patient tissues, such as, for example, in joints or the shoulder region, in which fatty tissue, aqueous tissue, and bone interact.

From the target field strength distribution, it is possible, using the laws of electrodynamics and the geometrical and electrical properties of an antenna apparatus, to determine a set of parameters by which radio frequency signals are determined. When generated by the radio frequency unit and transmitted by the antenna apparatus, the radio frequency signals generate a predetermined spatial dependency of the Larmor frequency. Using optimization methods such as least square root (LSR), an ideal spatial dependency of the Larmor frequency may be approximated under the boundary conditions such as number, frequency, and output of the radio frequency signals that may be generated and antenna elements of the antenna apparatus.

The magnetic resonance tomograph according to one or more of the present embodiments shares the advantages of the apparatus used and likewise of the method performed by the apparatus.

In an embodiment of the apparatus, the first frequency and the second frequency are symmetrical with the Larmor frequency. The Larmor frequency is defined as the precession frequency of the nuclear spins in the static magnetic field B0 without any influence of gradient fields or of radio frequency alternating magnetic fields. In the context of the present embodiments, a frequency pair is described as symmetrical with the Larmor frequency when the frequency values for the frequency pair F1, F2 are derived from a frequency deviation dF and the Larmor frequency LF by the equation F1=LF+dF and F2=LF−dF. A deviation from the frequencies F1, F2 according to the formula by less than 10 Hz, 100 Hz, 1 kHz, or 10 kHz is still assumed to be symmetrical.

Using a symmetrical frequency distribution, the determination of, for example, a linear gradient for the resulting from the Bloch-Siegert effect may be simplified.

In a possible embodiment of the apparatus, the antenna apparatus includes at least one first antenna element and a second antenna element. An antenna element may be, for example, an element of the antenna apparatus that is configured to be driven independently by the radio frequency unit with a radio frequency signal and configured to emit this signal to the examination region. The first antenna element is arranged symmetrical with the second antenna element with respect to a center of symmetry (e.g., the isocenter of a field magnet in the magnetic resonance tomograph). Symmetrical with the center of symmetry is seen in the context of the present embodiments as also including a mirror symmetry with a plane running through the center of symmetry, an axial symmetry with an axis running through the center of symmetry, or a point symmetry to the center of symmetry. However, a different arrangement in the examination region is also conceivable, in the form of a local coil, for example, which is essentially arranged symmetrical with the region that is to be examined, such as the head, knee, or other regions.

For example, two circular antenna coils may be arranged such that the examination subject is arranged between the antenna coils. A particularly linear frequency shift curve is created, for example, in the center between the two antenna coils when the ratio of distance to diameter is equal to the square root of 3/7 or roughly to the value 0.655.

The symmetry of the antenna elements makes it possible to determine in a simpler manner the field distribution and hence also the frequency shift in the Larmor frequency that is achieved with the Bloch-Siegert effect (e.g., when the antenna elements are also driven by frequencies that are shifted symmetrically with the Larmor frequency).

In an embodiment of the apparatus, the antenna apparatus includes a saddle-shaped coil.

A saddle-shaped coil allows a mechanical adjustment to curved surfaces and takes axial symmetries into account.

In a possible embodiment of the apparatus, the antenna apparatus includes a butterfly antenna.

A butterfly antenna may be an antenna the conductor of which is designed topologically as a figure eight (e.g., the antenna includes two adjacent conductor loops that are electrically connected by intersecting conductors). A butterfly antenna makes it possible to generate alternating magnetic fields deep within the examination subject. The alternating magnetic fields are orientated parallel to a plane in which the butterfly antenna is arranged. It is therefore possible, for example, to generate field components in a direction in which it is not possible for reasons of space to arrange facing pairs of coils in the style of a Helmholtz pair. With co-planar pairs consisting of a circular and a butterfly antenna, or those arranged in one plane, it is also conceivable, with appropriate phase-shifted activation, to generate a circularly polarized signal.

In one embodiment of the apparatus, the apparatus includes an antenna array. An antenna array may be a plurality of antenna elements, each of which has an independent signal feed. The plurality of antenna elements thus allows signals that differ in each case and with different amplitudes and/or phases and/or frequencies to be emitted at the same time. The antenna elements in the antenna array are spatially distributed (e.g., in a two- or three-dimensional matrix). In one embodiment, the different signals may be derived from one or a plurality of input signals by attenuator and/or phase-shift elements.

An antenna array makes it possible in the case of activation by different input signals through interference to generate spatial field distributions that may be controlled via the input signals.

In a possible embodiment of the apparatus, the antenna apparatus includes a third antenna element and a fourth antenna element that is arranged symmetrical to the center of symmetry (e.g., axis or point). The connecting line from the first antenna element to the second antenna element encloses an angle greater than 10 degrees with the connecting line between the third antenna element and the fourth antenna element.

The arrangement of the antenna elements in pairs that are arranged symmetrical with a center of symmetry and the connecting lines of which enclose an angle (e.g., are not in parallel) makes it possible, with appropriate activation by signals, to generate gradients of the Larmor frequency in different spatial directions using the Bloch-Siegert effect. The gradients in this way span a space for the spatial encoding.

In an embodiment of the apparatus, the antenna array includes two groups, each with a plurality of antenna elements. The antenna elements in a group are characterized by the fact that the antenna elements essentially have the same position along a first axis. "Essentially the same position" may be that the projections of the antenna elements all at least partly overlap alternately along a perpendicular onto the first axis. The groups may be arranged at different positions along the first axis (e.g., the projections of the antenna elements in one group do not overlap or only partly overlap with those in the other group). The first axis runs through the region being examined by the magnetic resonance tomograph (e.g., through the isocenter of the field magnet and essentially parallel with the B0 field direction of the field magnet).

The arrangement of groups of antenna elements along the first axis makes it possible, with appropriate activation of the antenna elements, for a field strength gradient to be generated along the axis and hence, through the Bloch-Siegert effect, to establish a gradient of the Larmor frequency along the axis. With appropriate activation of the antenna elements, it is possible to use these as a butterfly antenna.

In a possible embodiment of the apparatus, the antenna elements in a group are arranged along a curve that encloses the first axis. For example, the antenna elements may be arranged on a cylinder that encloses the examination region and the isocenter and in the center of which the first axis runs. In the context of the present embodiments, a curve may also be seen as a polygon or any intermediate shapes between a polygon and a circle, with two antenna elements in a group being, for example, arranged in each case symmetrical with the first axis, facing each other. In one embodiment, two antenna elements are arranged in each case facing each other in pairs with respect to the first axis, and two of these pairs are offset with each other around a circumferential angle of 90 degrees around the first axis.

The arrangement of the antenna elements along a closed curve around the first axis allows symmetrical irradiation in each case along different axes, which allows a particularly simple prediction of the field distribution of the alternating magnetic fields that have been generated and hence of the shift in the Larmor frequencies that may be generated therewith.

In a possible embodiment of the magnetic resonance tomograph, the radio frequency unit and/or the antenna apparatus has/have a safety device. The safety device is configured to protect the radio frequency unit in the event of simultaneous transmission of the transmission signal and of an excitation pulse or phase-encoding pulse. For example, the safety device may make the antenna apparatus or the radio frequency unit resonant on the first frequency and the second frequency of the radio frequency signal, such that a signal from an excitation pulse or a phase-encoding pulse is attenuated by more than 20 dB, 40 dB, 60 dB, or 100 dB at a signal output of the radio frequency unit for the radio frequency signal compared with a magnetic resonance tomograph without a safety device. It is likewise conceivable that a blocking circuit is provided as a safety device on the antenna apparatus and/or radio frequency unit. The blocking circuit is tuned to be resonant on the frequency of the excitation pulse or the phase-encoding pulse and suppresses this selectively by more than 20 dB, 40 dB, 60 dB, or 100 dB on a signal output of the radio frequency unit.

The safety device exploits the fact that for the Bloch-Siegert effect, a first frequency and second frequency that differ from the Larmor frequency of the nuclear spins to be examined in the B0 field of the magnetic resonance tomograph are to be used. Therefore, the safety device may protect the radio frequency unit in a frequency-selective way.

In an embodiment of the magnetic resonance tomograph, the Larmor frequency is lower than 10 MHz or lower than 5 MHz. The term Larmor frequency defines the precession frequency to be acquired at the field strength B0 of the field magnet. For protons at a field strength of 0.1 T, the Larmor frequency is approximately 4.257 MHz. It may therefore also be the magnetic field B0 for protons below 0.2 T or below 0.1 T. Hence, the frequency of the alternating magnetic field for generating the Bloch-Siegert effect, which is to be close to the Larmor frequency, is also lower.

The SAR load or temperature increase for the patient is lower at lower frequencies with the same radio frequency output, such that the alternating magnetic fields required for a spatial encoding using the Bloch-Siegert effect do not lead to the SAR limits being exceeded.

In a possible embodiment of the magnetic resonance tomograph, the radio frequency unit and the antenna apparatus are configured such as to generate a circularly polarized alternating magnetic field. For example, as antenna elements, the antenna apparatus may have hybrid pairs consisting of coil windings and butterfly coils arranged in a coplanar manner, which are driven by the radio frequency unit with two signals that are phase-shifted by 90 degrees. Different coils in a group or adjacent groups may be driven in an appropriate combination of the radio frequency unit by signals with a corresponding phase shift, such that these coils act as a butterfly coil. For example, two adjacent coils may be driven in antiphase.

This makes it possible to generate a circular polarization of the alternating fields with a planar antenna arrangement without enclosing the region to be examined. A circular excitation at the same SAR load achieves a stronger Bloch-Siegert effect compared with a linearly polarized excitation.

In an embodiment of the magnetic resonance tomograph, the scanner does not have any gradient coils or only has gradient coils for a spatial encoding in one or two coordinate axes.

With the apparatus according to one or more of the present embodiments, a spatial encoding may be achieved advantageously without a gradient coil for generating a magnetic field gradient, and thus, it is possible to dispense with some or all of the gradient coils.

DETAILED DESCRIPTION

Figure 1:
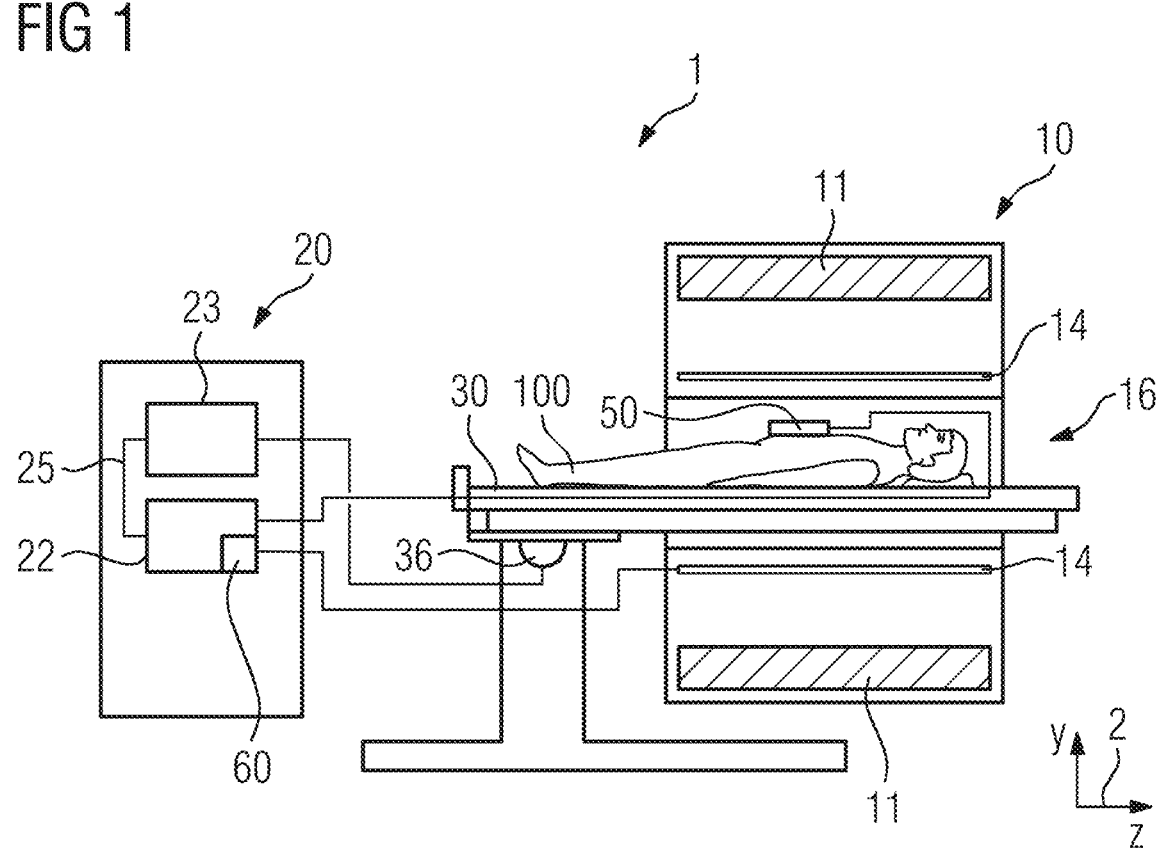
FIG. 1 shows an exemplary schematic representation of a magnetic resonance tomograph with an apparatus according to an embodiments for spatial encoding.

FIG. 1 shows a schematic representation of an embodiment of a magnetic resonance tomograph 1 with an apparatus 60 according to an embodiment for spatial encoding.

A magnet unit 10 has a field magnet 11 that generates a static magnetic field B0 for aligning nuclear spins of specimens or patients 100 in a recording region. The recording region is arranged in a patient tunnel 16 that extends in a longitudinal direction 2 through the magnet unit 10. A patient 100 may be moved into the data-recording area using a patient couch 30 and a positioning unit 36 of the patient couch 30. The field magnet 11 may be a superconducting magnet that may provide magnetic fields with a magnetic flux density of up to 3 T or higher (e.g., with the latest equipment). For lower field strengths, however, permanent magnets or electromagnets with normally conducting coils may also be used. Due to the lower absorption, spatial encoding using the Bloch-Siegert effect is particularly suitable for low Larmor frequencies and hence low B0 fields (e.g., below 1 T).

The magnet unit 10 also includes a body coil 14 that is configured to emit a radio frequency signal that is supplied via a signal line to the examination volume, and to receive resonance signals emitted by the patient 100 and emit the resonance signals over a signal line. However, the body coil 14 for the transmission of the radio frequency signal and/or receiving may be replaced by local coils 50 that are arranged in the patient tunnel 16 close to the patient 100. In one embodiment, the local coil 50 may be configured for transmitting and receiving, and therefore, a body coil 14 may be dispensed with.

A control unit 20 (e.g., a controller) supplies the magnet unit 10 with the signals for the body coil 14 and evaluates the signals that have been received. A magnetic resonance tomograph control 23 coordinates the sub-assemblies.

The control unit 20 includes a radio frequency unit 22 that is configured to generate a radio frequency pulse with a predetermined chronological sequence, amplitude, and spectral output distribution for exciting a magnetic resonance of the nuclear spins in the patient 100. Pulse outputs in the kilowatt region may be achieved. The individual units are connected to one another via a signal bus 25.

The radio frequency signal generated by the radio frequency unit 22 is supplied via a signal connection to the body coil 14 and transmitted to the body of the patient 100 to excite the nuclear spins there. Emission of the radio frequency signal via one or a plurality of coil windings of the local coil matrix 50 may also be provided.

In a method according to one or more of the present embodiments, for the radio frequency unit 22 and an antenna apparatus, a separate antenna apparatus may be used for spatial encoding of the nuclear spins for spatial encoding using the Bloch-Siegert effect. Depending on the sequence used, the same units, such as oscillators and output amplifiers of the radio frequency unit 22, may be used for excitation and spatial encoding if these ensue one after the other according to the sequence. The body coil 14 and/or the local coil 50 may be used; in one embodiment, however, antenna apparatuses with special properties, as described with respect to the following figures, are provided. These antenna apparatuses may be arranged in the housing of a local coil matrix 50 (e.g., with dedicated, separate coil windings). This may be the case, for example, in a head coil or a knee coil. More detail of the Bloch-Siegert effect and of the acquisition of the signals required for spatial encoding is set out hereafter with respect to the method according to one or more of the present embodiments.

The local coil matrix 50 may then receive a magnetic resonance signal from the body of the patient 100 because, due to the limited distance, the signal-to-noise ratio (SNR) of the local coil 50 is better than in the case of reception by the body coil 14. The MR signal received by the local coil matrix 50 is prepared in the local coil 50 and forwarded to the radio frequency unit 22 of the magnetic resonance tomograph 1 for evaluation and image acquisition. The signal connection may be used for this purpose, but it is also conceivable, for example, to use wireless transmission.

Figure 2:
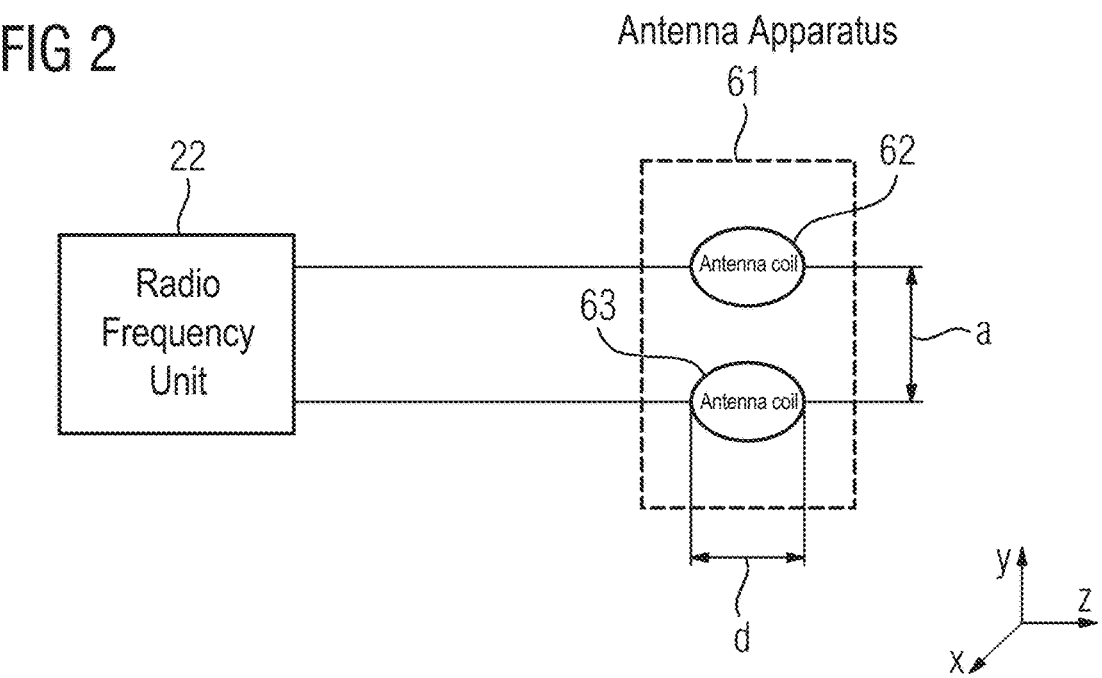
FIG. 2 shows an antenna apparatus of an embodiment of an apparatus for spatial encoding.

FIG. 2 shows an exemplary embodiment of an apparatus 60 for performing the method. The apparatus for spatial encoding shown in FIG. 2 uses transmission channels of a radio frequency unit 22 of the magnetic resonance tomograph 1. In one embodiment, however, the apparatus may have a separate radio frequency unit, yet it is necessary for the radio frequency unit 22 to have a plurality of oscillators and amplifiers for generating a plurality of radio frequency signals. Due to the separate oscillators, signals of different frequency and phase may be generated independent of one another. The separate amplifier makes it possible to also set the amplitude independently. An oscillator combined with the amplifier that is in signal connection therewith is referred to below as a transmission channel. The radio frequency unit 22 with the transmission channels may also be used to excite the nuclear spins, for example, in a pTX magnetic resonance tomograph.

The embodiment of the apparatus 60 that is shown in FIG. 2 includes antenna coils as antenna elements. Other antenna elements, such as dipoles, may also be provided, however. The radio frequency signals generated by the radio frequency unit 22 are forwarded to a first antenna coil 62 and a second antenna coil 63 via a signal connection. In one embodiment, a switch matrix that makes it possible to create a signal connection in a flexible manner between the radio frequency unit 22 and the antenna coil 62, 63 is provided between the radio frequency unit 22 and the antenna apparatus 61, such that the transmission channels may also be used in a flexible manner for excitation for a local transmission coil. The radio frequency signal is converted by the first antenna coil 61 and the second antenna coil 62 into a magnetic radio frequency alternating field that is radiated into the examination region between the antenna coils 62, 63.

In one embodiment, however, the switch matrix includes adjustable or connectable phase shifters and/or adders and/or attenuators, which make it possible to combine the input signals from the radio frequency unit 22 into different new signals with a variable phase and amplitude. The number of signals generated and hence likewise the number of antenna coils that may be supplied with a signal may be greater than the number of transmission channels in the radio frequency unit 22. The switch matrix may also be part of the antenna apparatus 61, such that fewer signal connections are required between the radio frequency unit 22 in the MRT housing and in the antenna apparatus 61 that is arranged on the patient.

FIG. 2 shows a particularly advantageous configuration according to one or more of the present embodiments of the antenna coils 62, 63, in which a circular first antenna coil 62 and a circular second antenna coil 63 face each other and are spaced apart. In one application according to one or more of the present embodiments, the two antenna coils 62, 63 are arranged in the examination region or FoV of the field magnet 11. The two antenna coils 62, 63 are arranged in two essentially level and essentially parallel planes, with the patient or the region to be examined being arranged between the first antenna coil 62 and the second antenna coil 63. Using the Bloch-Siegert effect, an encoding in the direction of the y-axis may be achieved with such an arrangement. For a ratio of the distance a to the diameter d of the antenna coils 62, 63 of 0.655, this results in an almost linear gradient, shown below in FIG. 3, of the Larmor frequency, according to the y-coordinate. This gradient simplifies image reconstruction.

Figure 3:
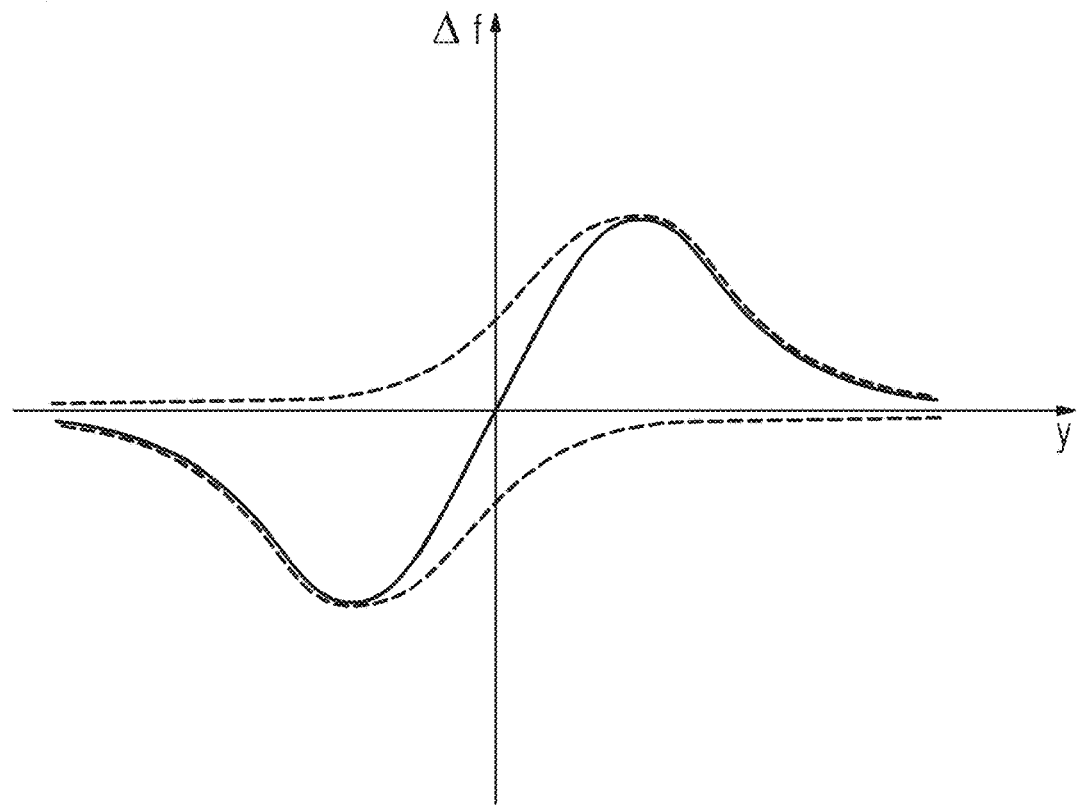
FIG. 3 shows an exemplary spatial curve of a frequency shift that may be achieved with the apparatus according to an embodiment.

FIG. 3 shows a corresponding curve of the frequency shift as a function of the y-coordinate. The axis denoted by Δf indicates the frequency shift of the Larmor frequency. The first antenna coil 62 is driven by a radio frequency signal, which is equal to LF (Larmor frequency with no shift) plus a frequency deviation dF; the second antenna coil 63 is driven by a radio frequency signal, the frequency of which is equal to LF minus the frequency deviation dF. The dotted lines indicate the effect achievable in each case by one of the antenna coils 61, 62; the continuous line indicates the effect resulting from the two antenna coils 61, 62. Both control signals have the same amplitude, yet dF is greater than the target frequency shift Δf, since with the Bloch-Siegert effect, the amplitude is squared. At the coordinate origin, the Larmor frequency is equal to the Larmor frequency in the static magnetic field B0 without an external radio frequency field, since due to the symmetry of the arrangement and of the signals, the effect is cancelled out precisely in the center.

A spatial encoding according to one or more of the present embodiments in a second axis (e.g., the x-axis in FIG. 2) may be achieved by a further pair of antenna coils that face each other in the same way along the x-axis.

If it is not possible to provide two facing circular antenna coils 62, 63, for example, because the patient's body or a limb extends along the axis, then according to one or more of the present embodiments, two coils known as butterfly coils may be used. The term butterfly coil denotes coils, in which the conductor loop is shaped as a figure of eight or two conductor loops, when the coils have a plurality of windings, are electrically connected to each other at least via crossed conductors, such that the directions of the current in the two conductor loops that are arranged adjacent to each other run in opposite directions. As a result thereof, at a deep level (e.g., at a distance perpendicular to the plane in which the conductor loops are arranged), a field component that is parallel to the plane is generated (e.g., in the plane of symmetry of the two conductor loops) in the center between the conductor loops.

The Bloch-Siegert effect is at its maximum when the field vectors of the alternating magnetic field for generating the Bloch-Siegert effect are perpendicular to the direction of the field B0 that aligns the nuclear spins. In the exemplary diagrams shown in the figures, the B0-field is aligned along the z-axis, such that the components of the alternating magnetic field for generating the Bloch-Siegert effect may be in the x-y plane. To carry out spatial encoding in the z-direction, the field vector of the target alternating magnetic fields is also to be in the x-y-plane. However, with respect to the amplitude of the alternating fields, a gradient is to be generated along the z-axis in order to obtain different Larmor frequencies along the z-axis and hence to achieve spatial encoding along the z-axis.

To generate a gradient of the Larmor frequency along the z-axis, for example, two pairs of coils that each face the other may then be arranged adjacent to each other at spaced positions along the z-axis. One pair generates in each case a homogeneous field strength in a plane perpendicular to the z-axis, in an arrangement that is comparable with a Helmholtz pair of coils. The one pair is driven by a radio frequency signal with the frequency LF+dF, and the second pair of facing coils is driven by a radio frequency signal with the frequency LF−dF. Due to the declining field strength laterally along the z-axis, this then results in a different Bloch-Siegert effect and hence in a variation in the Larmor frequency along the z-axis. The two pairs work together again as shown in FIG. 3 and in a region between the pairs along the z-axis, generate a virtually linear curve for the variation in the Larmor frequency.

In one embodiment, instead of a linearly polarized alternating magnetic field generated by a single pair of coils, a circularly polarized field may be used for spatial encoding by the Bloch-Siegert effect. This has the advantageous effect that the SAR-load for the same strength of spatial encoding may be halved compared with linear polarization. A circular polarization may be achieved according to one or more of the present embodiments by arranging a combination of a circular antenna coil and a butterfly coil one on top of the other in a coplanar manner instead of a single circular antenna coil or butterfly coil. If these two coils are then driven by radio frequency signals, which are phase-shifted by only 90 degrees but may have the same amplitude and frequency, then corresponding circularly polarized alternating magnetic fields may be provided for spatial encoding according to one or more of the present embodiments.

To also generate a circular polarization as shown below with respect to FIG. 4 and FIG. 5, two coil pairs may be arranged in each case in a plane (e.g., in an x-y orientation), such that the connecting lines of the two coils in the pair intersect at an angle of, for example, 90 degrees between the coils. When the pairs are driven by a signal with a 90-degree phase shift between the pairs, the result is then an alternating magnetic field with circular polarization between the coils.

Basically, according to one or more of the present embodiments, the antenna coils may be configured not only to be planar but, for example, according to the geometry of a patient tunnel, as a saddle-shaped arrangement on a cylindrical body. Other geometries that are suitable for arrangement on or in different local coils 50, such as head or knee coils, may also be provided.

Figure 4:
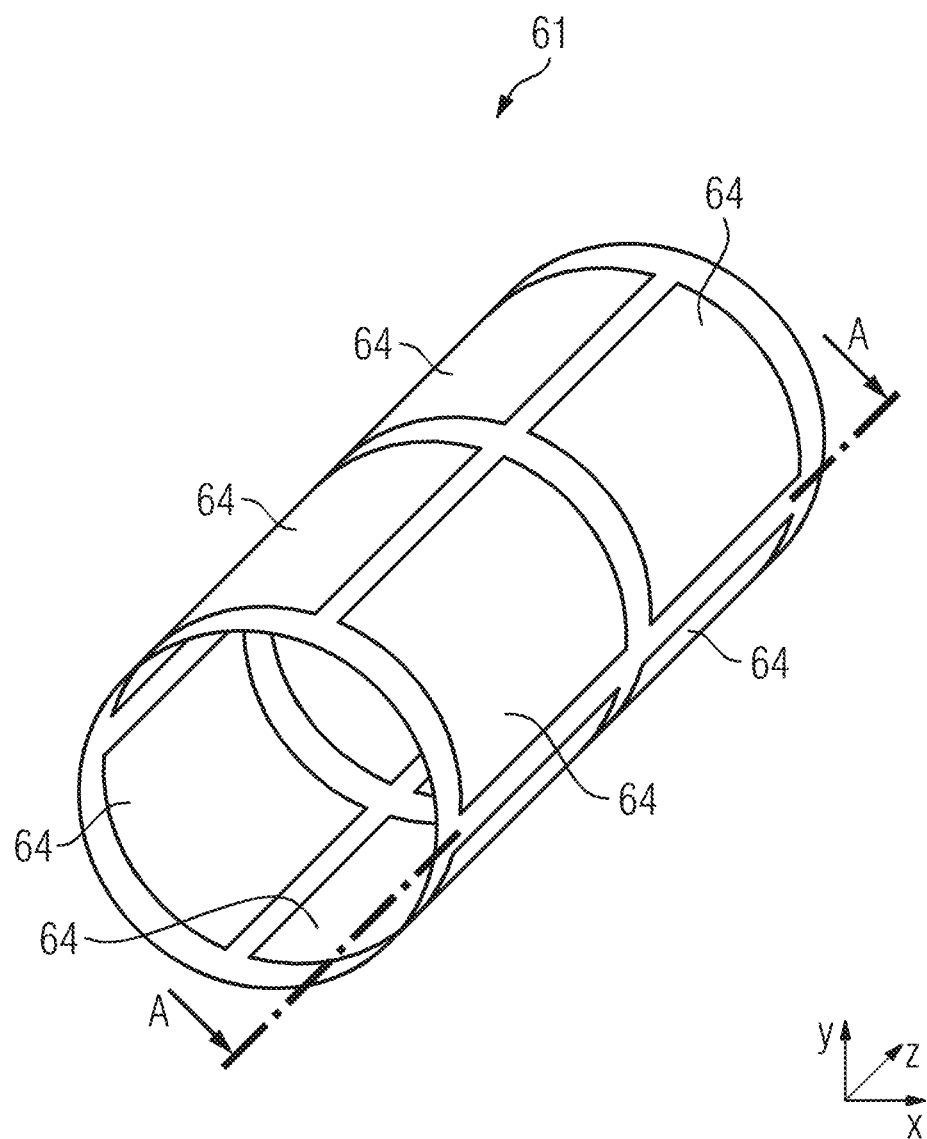
FIG. 4 shows an antenna apparatus of an embodiment of an apparatus for spatial encoding.

FIG. 4 shows an embodiment of an antenna apparatus 61 of an apparatus for spatial encoding according to one or more of the present embodiments. A plurality of antenna coils 54 are arranged in a network/matrix or array on the side of or on top of a support that is in the form of a cylinder. Other shapes such as, for example, cuboids, prisms, or ellipsoids or geometries predetermined by a body shape that is to be examined may also be provided. The support for the antenna coils may be provided, for example, by the wall of the patient tunnel or by a local coil housing. A self-supporting antenna apparatus 61 such as, for example, a birdcage antenna, with the antenna coils 64 being provided by individual segments of the birdcage antenna, may also be provided. The antenna coils 64 may be driven independently of each other and with different radio frequency signals.

The antenna coils 64 are, for example, arranged in two groups along the z-axis, the two groups being spaced apart. The individual antenna coils 64 in one group are in turn arranged along the entire circumference of the support, such that the circumference of the antenna coils 64 is covered without any substantial gaps. In other words, the distance between two adjacent antenna coils 64 in a group is smaller than the extent of the respective antenna coils 64 along the circumference. Yet, it is also conceivable that adjacent antenna coils 64 in a group overlap, for example, in order to decouple these inductively from one another.

In each case, two of the antenna coils 64 are arranged in pairs symmetrical with the axis of symmetry of the support, parallel to the z-axis, such that the two respective antenna elements 64 are facing each other with respect to the axis of symmetry. When a pair is driven by radio frequency signals of the same amplitude, but different plus/minus signs for the frequency shift with respect to the Larmor frequency, then an almost linear gradient of the resulting Larmor frequency may therefore be achieved along the connecting line for the two antenna coils 64 in the pair using the Bloch-Siegert effect. In FIG. 4, two pairs of antenna coils 64 are provided in a group in each case, with the connecting lines for the two pairs being perpendicular one above the other. However, different arrangements of antenna coils 64 in a group may be provided (e.g., with 3, 4 or more pairs of antenna coils that are arranged symmetrical with one another).

The antenna arrangement in FIG. 4 allows spatial encoding of the Larmor frequency in all three spatial directions through the arrangement of the antenna coils 64 with activation in an appropriate manner.

Figure 5:
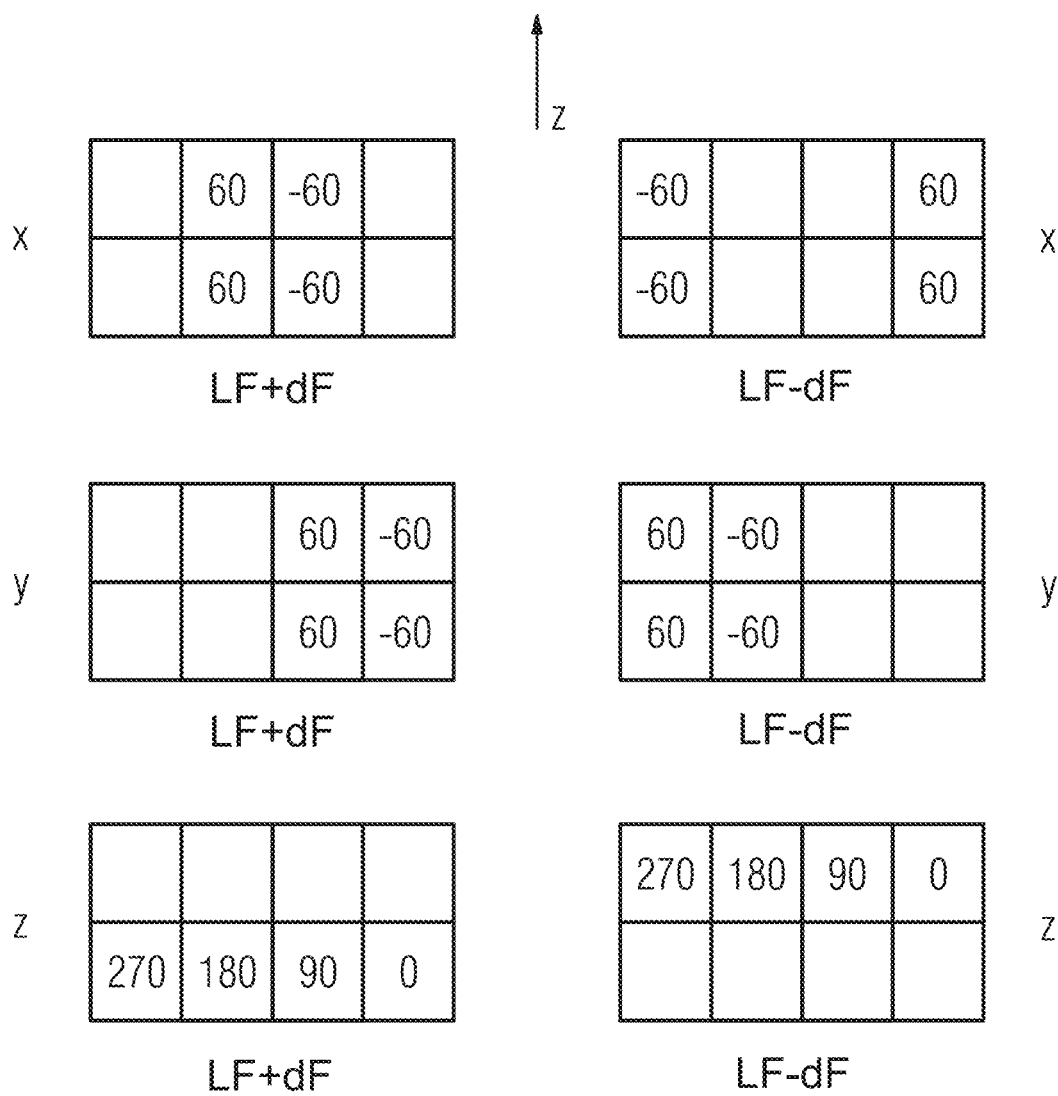
FIG. 5 shows a two-dimensional schematic projection of an antenna apparatus according to an embodiment.

To give a clear overview, FIG. 5 shows the antenna apparatus as a two-dimensional projection. The support is cut open and unrolled along the line A-A in FIG. 4. The arrow z indicates the direction of the static magnetic field B0.

A total of six diagrams of the unrolled antenna matrix are set out in two columns and three lines. The letters x, y and z on the left and right beside the diagram of the coil matrix indicate the axis along which a gradient of the Larmor frequency is meant to be generated, from top to bottom along the x-axis, along the y-axis, and along the z-axis.

The two columns indicate which signal is to be applied to the respective antenna coil 64. In the left-hand column is the signal with the Larmor frequency LF plus a frequency deviation dF, characterized in each case by (LF+dF). In the right-hand column is the signal with the Larmor frequency LF minus a frequency deviation dF, characterized in each case by (LF−dF).

In the box for the respective antenna coil, the number shows the phase shift that the connected signal is supposed to have. The number indicated is expressed in degrees relating to a randomly selected zero point for all the signals in a frequency. Empty boxes indicate that no signal is connected to the respective frequency. For these antenna coils, the signal for the other frequency is connected, as set out in the other column.

The phase shifts are provided such that in each case, the phase shifts generate a field with circular polarization and minimal SAR.

The direction of the gradient of the Larmor frequency along an axis may be reversed by transposing the frequencies LF+dF and LF−dF for the connected signals, which is equivalent to transposing the diagrams of the antenna matrix from the left-hand column and the right-hand column in FIG. 5.

The phase shifts may be achieved with switchable phase-shifters, such that with two oscillators and two output amplifiers for frequencies LF+−dF and one phase-shifter each for 90 degrees, 180 degrees, and 270 degrees and two phase-shifters each for +60 degrees and minus 60 degrees, all the gradients may be achieved. This allows, for example, the use of particularly efficient output amplifiers of classes D and E, which operate in the non-linear region of the amplifier elements.

However, other combinations with a plurality of groups and pairs may also be provided, allowing with an appropriate activation pattern, a spatial encoding using the Bloch-Siegert effect in at least three directions that together make up a space.

Figure 6:
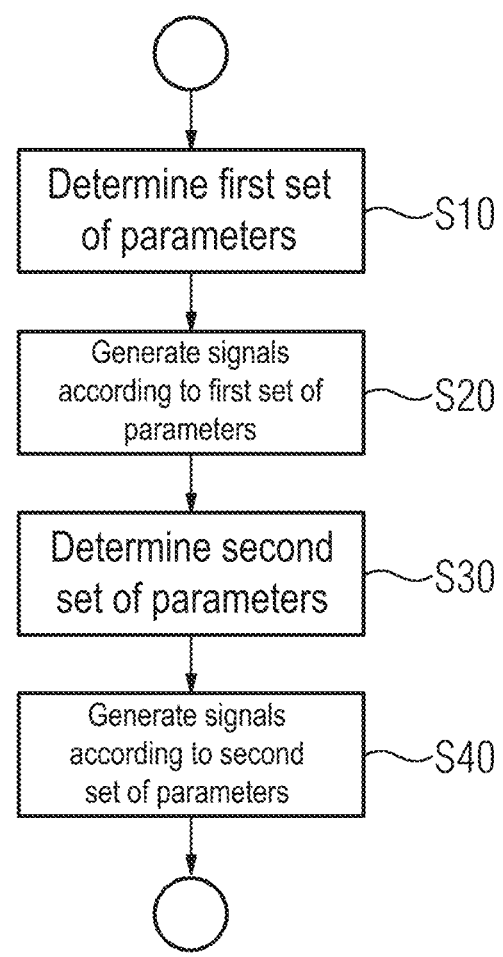
FIG. 6 shows a schematic flow chart of a method according to an embodiment.

FIG. 6 shows a method according to one or more of the present embodiments for generating spatial encoding using the Bloch-Siegert effect and the apparatus according to one or more of the present embodiments as a flow chart.

In act S10, a first set of parameters consisting of a first frequency and a first amplitude and a second frequency and a second amplitude is determined by the magnetic resonance tomograph. When transmitting signals according to the parameters in the first set of parameters via the antenna apparatus 61, the magnetic resonance tomograph generates a first gradient above the Larmor frequency of the nuclear spins using the Bloch-Siegert effect. From a desired gradient, a required field strength, for example, may then be achieved using the known dependence of the Bloch-Siegert effect on the field strength and on the frequency of the alternating magnetic field at a known frequency. A required amplitude and phase of the drive signals for the antenna coils 64 may be determined from the laws of electrodynamics and the geometry of the antenna apparatus 61. This may be achieved by approximation methods (e.g., such as those also used to calculate SAR loads or for RF shimming). See also the introduction to the description.

In act S20, signals are generated according to the first set of parameters by the radio frequency unit 22 and transmitted to the examination region by the antenna apparatus 61.

In the same way, in act S30, a second set of parameters from a third frequency and a third amplitude and a fourth frequency and a fourth amplitude are determined by the magnetic resonance tomograph, such that when transmitting signals according to the second set of parameters via the antenna apparatus 61, a second gradient is generated using the Bloch-Siegert effect above the Larmor frequency of the nuclear spins. The first set of parameters and the second set of parameters differ in at least the first frequency and/or the first amplitude and/or the second frequency and/or the second amplitude of the first set from the third frequency and/or the third amplitude and/or the fourth frequency and/or the fourth amplitude of the second set, respectively.

In act S40, signals are generated according to a second set of parameters using the radio frequency unit 22, and transmitted to the examination region using the antenna apparatus 61.

For example, using the first set of parameters, a spatial encoding along the x-axis may be generated; using the second set of parameters, a spatial encoding along the y-axis may be generated if signals are transmitted by the antenna apparatus in FIG. 4 using the phase shift shown in FIG. 5. The acts S10 and S30 to determine the sets of parameters use a predetermined table or approximation formula, such that the magnetic resonance tomograph 1 is not required during image acquisition. The complex calculations of the field distribution may also then be performed in advance on other computation units, and the result may be stored on the magnetic resonance tomograph in the form of the table or approximation formula. An optimization method in which, for example, magnetic resonance measurements are entered into a phantom may also be provided.

Although the invention has been illustrated and described in greater detail by the exemplary embodiment, the invention is not restricted to the examples described. Other variants may be derived therefrom by a person skilled in the art without going beyond the scope of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An apparatus for spatial encoding in magnetic resonance tomography with a magnetic resonance tomograph, the apparatus comprising:
   a radio frequency (RF) unit configured to generate a first RF signal with a first frequency and a second RF signal with a second frequency with a high output, wherein the first frequency and the second frequency are close to a Larmor frequency of the magnetic resonance tomograph, and the first frequency is not equal to the second frequency, and wherein the first frequency and the second frequency are symmetrical with the Larmor frequency; and
   an antenna apparatus configured to emit the first RF signal and the second RF signal in an examination region of the magnetic resonance tomograph.

2. The apparatus of claim 1, wherein the antenna apparatus comprises a first antenna element and a second antenna element, and
   wherein the first antenna element is arranged symmetrical with the second antenna element with respect to a center of symmetry.

3. The apparatus of claim 2, wherein the antenna apparatus further comprises a third antenna element and a fourth antenna element that is arranged symmetrical with the center of symmetry,
   wherein a connecting line from the first antenna element to the second antenna element encloses an angle greater than 10 degrees with a connecting line between the third antenna element and the fourth antenna element.

4. The apparatus of claim 1, wherein the antenna apparatus comprises a saddle-shaped coil.

5. The apparatus of claim 1, wherein the antenna apparatus comprises a butterfly antenna.

6. The apparatus of claim 1, wherein the antenna apparatus comprises an antenna array.

7. The apparatus of claim 6, wherein the antenna array comprises two groups, each of the two groups having a plurality of antenna elements, and
   wherein the two groups are arranged at different positions along a first axis.

8. The apparatus of claim 7, wherein the plurality of antenna elements are arranged in a group along a curve that encloses the first axis.

9. The apparatus of claim 1, wherein the RF unit, the antenna apparatus, or the RF unit and the antenna apparatus comprise a safety device configured to protect the radio frequency unit when transmitting a transmission signal and an excitation pulse at the same time.

10. A magnetic resonance tomograph comprising:
    an apparatus for spatial encoding in magnetic resonance tomography with a magnetic resonance tomograph, the apparatus comprising:
       a radio frequency (RF) unit configured to generate a first RF signal with a first frequency and a second RF signal with a second frequency with a high output, wherein the first frequency and the second frequency are close to a Larmor frequency of the magnetic resonance tomograph, and the first frequency is not equal to the second frequency; and
       an antenna apparatus configured to emit the first RF signal and the second RF signal in an examination region of the magnetic resonance tomograph,
    wherein the magnetic resonance tomograph is configured to:
       determine a first set of parameters from the first frequency and a first amplitude, and from the second frequency and a second amplitude, such that when signals are transmitted according to parameters in the first set of parameters via the antenna apparatus, a first gradient of a Larmor frequency of nuclear spins is generated by the Bloch-Siegert effect; and
       generate the first RF signal and the second RF signal according to the first set of parameters using the radio frequency unit; and
       transmit the first RF signal and the second RF signal to the examination region using the antenna apparatus for spatial encoding of the nuclear spins.

11. The magnetic resonance tomograph of claim 10, wherein the magnetic resonance tomograph does not have any gradient coils or only has gradient coils for spatial encoding in one or two coordinate axes.

12. The magnetic resonance system of claim 10, wherein the Larmor frequency is lower than 10 MHz.

13. The magnetic resonance tomograph of claim 10, wherein the radio frequency unit and the antenna apparatus are configured to generate a circularly polarized alternating magnetic field.

14. A method for operating a magnetic resonance tomograph and a radio frequency unit, the method comprising:
    determining, by the magnetic resonance tomograph, a first set of parameters from a first frequency and a first amplitude, and from a second frequency and a second amplitude, such that during transmission of signals according to parameters in the first set of parameters via an antenna apparatus, a first gradient above the Larmor frequency of nuclear spins is generated by the Bloch-Siegert effect;
    generating signals according to the first set of parameters using a radio frequency unit;
    transmitting the signals generated according to the first set of parameters to an examination region by the antenna apparatus;
    determining a second set of parameters from a third frequency and a third amplitude, and from a fourth frequency and a fourth amplitude by the magnetic resonance tomograph, such that during transmission of signals according to parameters in the second set of parameters via the antenna apparatus, a second gradient above the Larmor frequency of the nuclear spins is generated by the Bloch-Siegert effect, wherein the first set of parameters and the second set of parameters differ at least in the first frequency, the first amplitude, the second frequency, the second amplitude, or any combination thereof of the first set of parameters from the third frequency, the third amplitude, the fourth frequency, the fourth amplitude, or any combination thereof of the second set of parameters, respectively;

generating signals according to the second set of parameters using the radio frequency unit; and transmitting the signals generated according to the second set of parameters to the examination region using the antenna apparatus.

15. The method of claim 14, wherein the transmitting of the signals generated according to the first set of parameters ensues at a same time as the transmitting of the signals generated according to the second set of parameters.

16. The method of claim 14, wherein the first frequency and the second frequency are symmetrical with the Larmor frequency, the third frequency and the fourth frequency are symmetrical with the Larmor frequency, or a combination thereof.

17. The method of claim 14, wherein the antenna apparatus comprises a first antenna element and a second antenna element, and
wherein the first antenna element is arranged apart from the second antenna element.

18. An apparatus for spatial encoding in magnetic resonance tomography with a magnetic resonance tomograph, the apparatus comprising:

a radio frequency (RF) unit configured to generate a first RF signal with a first frequency and a second RF signal with a second frequency with a high output, wherein the first frequency and the second frequency are close to a Larmor frequency of the magnetic resonance tomograph, and the first frequency is not equal to the second frequency; and an antenna apparatus configured to emit the first RF signal and the second RF signal in an examination region of the magnetic resonance tomograph, wherein the antenna apparatus comprises a first antenna element and a second antenna element, and wherein the first antenna element is arranged symmetrical with the second antenna element with respect to a center of symmetry.

* * * * *